United States Patent [19]

Friesz et al.

[11] Patent Number: 4,820,838

[45] Date of Patent: Apr. 11, 1989

[54] PROCESS FOR THE PREPARATION OF DEPOGEN

[75] Inventors: Antal Friesz; Zsuzsanna Nad, Both of Budapest; Lajos Nagy, Szentendre; Tamas Kallay, Budapest, all of Hungary

[73] Assignee: Chinoin Gyogyszer- Es Vegyeszeti Termekek Gyara Rt., Budapest, Hungary

[21] Appl. No.: 912,997

[22] Filed: Sep. 26, 1986

[30] Foreign Application Priority Data

Oct. 3, 1985 [HU] Hungary .............................. 3831/85

[51] Int. Cl.$^4$ .................... C07D 473/08; A61K 31/52
[52] U.S. Cl. .................................... 544/268; 544/267
[58] Field of Search ................ 544/267, 268; 514/263, 514/265

[56] References Cited

U.S. PATENT DOCUMENTS 4,035,366  7/1977  Szentmiklösi et al. ............. 260/253

FOREIGN PATENT DOCUMENTS 968534  2/1958  Fed. Rep. of Germany .
2975    9/1963  France .

Primary Examiner—Nicolas S. Rizzo
Attorney, Agent, or Firm—Herbert Dubno; Jonathan Myers

[57] ABSTRACT

The invention relates to a process for the preparation of a new crystalline monohydrate of 1-(3', 4'-diethoxy-benzyl-6, 7-diethoxy-3,4-dihydro-isoquinolinium-theophylline-7-acetate and if desired of pure 1-(3', 4'-diethoxy-benzyl)-6,7-diethoxy-3, 4-dihydro-isoquinolinium-theophylline-7-acetate free of contaminating oxidation products which comprises reacting 1-(3',4'-diethoxy-benzyl)-6,7-diethoxy-3,4-dihydro-isoquinolinium with theophylline-7-acetate acid in the presence of water and one or more organic solvent(s) and if desired dehydrating the 1-(3',4'-diethoxy-benzyl) 6,7-diethoxy-3,4-dihydro-isoquinolinium-theophylline-7-acetate-monohydrate thus obtained.

13 Claims, No Drawings

PROCESS FOR THE PREPARATION OF DEPOGEN

This invention relates to a process for the preparation of 1-(3',4'-diethoxy-benzyl)-6,7-diethoxy-3,4-dihydro-isoquinolinium-theophylline-7-acetate of high purity and the new crystalline monohydrate thereof.

According to a further aspect of the present invention there is provided the new crystalline monohydrate of 1-(3',4'-diethoxy-benzyl)-6,7-diethoxy-3,4-dihydro-isoquinolinium-theophylline-7-acetate.

It is known that salts of various tetrahydro-isoquinoline derivatives formed with theophylline-7-acetic acid possess valuable therapeutical properties. The said salts exhibit particularly valuable blood pressure-decreasing, respiration stabilizing and spasmolytic effect and the general activity increasing effect exerted on the organism is significant as well (Hungarian Pat. No. 167,246).

The salt of 1-(3',4'-diethoxy-benzyl)-6,7-diethoxy-3,4-dihydro-isoquinoline (referred to furtheron as No-Spa base) formed with theophylline-7-acetic acid proved to be particularly effective and is a well-known gerontological drug named Depogen.

Only a single process is known for the preparation of 1-(3',4'-diethoxy-benzyl)-6,7-diethoxy-3,4-dihydro-isoquinolinium-theophylline-7-acetate (referred to furtheron as Depogen) whereby equimolar amounts of No-Spa base and theophylline-7-acetic acid are reacted in an alcohol (preferably ethanol or isopropanol) and the solid precipitated on cooling is filtered off. (Hungarian Pat. No. 167,246).

It is well-known that while No-Spa-hydrochloride is a stable compound, the base set free from this salt is unstable. The No-Spa base is particularly sensitive towards oxidation and even slight oxidizing agents (e.g. the oxygen of air) can give rise to the formation of by-products of different degrees of oxidation. The said high oxidative activity is due to the very high sensitivity of the methylene bridge of the benzyl group towards oxidation.

In the course of the first step of the preparation of Depogen the No-Spa base is set free from the hydrochloride thereof. The base thus set free is unstable until the theophylline-7-acetic acid salt thereof is formed. Practical experience has shown that so far is has not been possible to quench the oxidation of No-Spa base and for this reason crystallization of Depogen takes place in a reaction mixture comprising a considerable amount of by-product. The complete removal of the by-products is rendered very difficult by the fact that Depogen can be but very poorly purified by recrystallization; this is attributable to the presence of structurally strictly related by-products and the loose crystal structure of Depogen (Depogen prepared according to Hungarian Pat. No. 167,246 contains contaminations in an amount of 3–5%).

It is the object of the present invention to provide a process which eliminates and overcomes the above difficulties.

The present invention is based on the surprising recognition that if the reaction of No-Spa base and theophylline-7-acetic acid is carried out in a suitable water-containing solvent, the readily crystallizable pure monohydrate of Depogen is obtained. The said crystalline monohydrate is a new compound which can be converted into Depogen by removal of the crystal water.

The present invention relates to an improved process for the preparation of pure 1-(3',4'-diethoxy-benzyl-)-6,7-diethoxy-3,4-dihydro-isoquinolinium-theophylline-7-acetate free of contaminating oxidation products by reacting 1-(3',4'-diethoxy-benzyl)-6,7-diethoxy-3,4-dihydro-isoquinoline with theophylline-7-acetic acid which comprises forming at first the crystalline monohydrate of 1-(3',4'-diethoxy-benzyl)-6,7-diethoxy-3,4-dihydro-isoquinolinium-theophylline-7-acetate, removing the contaminating oxidation products by washing and removing crystal-water from the pure crystalline 1-(3',4'-diethoxy-benzyl)-6,7-diethoxy-3,4-dihydro-isoquinolinium-theophylline-7-acetate-monohydrate thus obtained.

According to further aspect of the present invention there is provided a process for the preparation of the crystalline monhydrate of 1-(3',4'-diethoxy-benzyl)-6,7-diethoxy-3,4-dihydro-isoquinolinium-theophylline-7-acetate which comprises reacting 1-(3',4'-diethoxy-benzyl)-6,7-diethoxy-3,4-dihydro-isoquinoline with theophylline-7-acetic acid in the presence of water and one or more organic solvent(s), crystallizing the crystalline monohydrate of 1-(3',4'-diethoxy-benzyl)-6,7-diethoxy-3,4-dihydro-isoquinolinium-theophylline-7-acetate—optionally after addition of a further solvent and separating the said product from the contaminating oxidation by-products being in the solution by filtration.

The essential feature of the improved preparation of Depogen according to the present invention resides in the presence of water and an organic solvent. It is preferred to use organic solvents unrestrictidly miscible with water. Thus it is particularly preferred to use ketones and alcohols, especially acetone and isopropanol. If in the course of the formation of the No-Spa base an organic solvent is used which is different from the solvent applied in the preparation of Depogen, one may proceed preferably by removing the excess of the solvent by distillation and carrying out crystallization of Depogen-monohydrate in a mixture of water and a water-miscible solvent.

Dehydration of Depogen-monohydrate can be accomplished by several methods. One may proceed by removing crystal-water in vacuo by thermal treatment. One may also proceed by dissolving Depogen-monhydrate under warming in an anhydrous solvent suitable for recrystallization and thereafter cooling the solution to yield the product free of crystal water. For this purpose solvents may be used in which Depogen is soluble but to a limited extent. According to this form of realization of the process dehydration requires a longer time.

Further details of the present invention are to be found in the following Examples without limiting the scope of protection to the said Examples.

EXAMPLE 1

Preparation of the crystalline monohydrate of 1-(3',4'-diethoxy-benzyl)-6,7-diethoxy-3,4-dihydro-isoquinoline-theophylline-7-acetate (referred to furtheron as Depogen.H$_2$O)

Into a 1000 ml three-necked flask equipped with a stirrer 104.16 g m (0,235 mole) of No-Spa hydrochloride, 160 ml of dichloromethane and 160 ml of water are weighed in. Under stirring a clear solution is formed. A solution of 11.2 g of solid sodium hydroxide and 224 ml of water is added and stirring is continued for a further period of 15 minutes. The phases are separated, the aqueous layer is extracted with 40 ml of dichloro methane and the dichloro methane phases are united.

Into a 2000 ml four-necked flask equipped with a stirrer and a distillation head 54.4 g (0.228 mole) of theophylline-7-acetic acid, 960 ml of acetone and 80 ml of water was introduced. The dichloro methane solution prepared according to the previous pharagraph is added under stirring and the reaction mixture is heated to boiling under stirring. Distillation of dichloromethane begins. Distillation is continued until the temperature of the vapour reaches the value of 57° C. During distillation the dichloromethane is replaced by an equal volume of acetone. After distillation the hot solution is filtered and slowly added to 480 ml of acetone (15°-20° C.) under cooling and stirring. When one-third of the solution has been added, the crystallized product is stirred for 10-15 minutes and the residual amount of the hot reaction mixture is poured in afterwards. The addition having been completed the crystalline paste is stirred at 15°-20° C. for 2 hours and allowed to stand at 0° C. for 12 hours. The product is filtered off, washed twice with 200 ml of 92% aqueous acetone each and dried. Thus 142 g of the desired compound are obtained in the form of yellowish white crystals, yield 95.5%. The structure of the product is confirmed by analysis, determination of the water content, IR-spectrum and determination of the crystal structure.

Analysis: Calc.: C%=60.63; H%=6.63; N%=10.71; O%=22.03; Found: C%=60.61; H%=6.62; N%=10.67; O%=22.10.

EXAMPLE 2

Into a 500 ml three-tube flask equipped with a stirrer 80 ml of a 20% sodium hydroxide solution, and 80 ml of methyl ethyl ketone are weighed in whereupon at 40° C. 43.4 g (0.1 mole) of No-Spa-hydrochloride are added and the mixture is stirred until the solid material is dissolved. The phases are separated, the aqueous layer is extracted with 20 ml and 10 ml of methyl ethyl ketone.

335 ml of methyl ethyl ketone, 20 ml of water and 22.6 g (0.095 mole) of theophylline-7-acetic acid are weighed in a 1000 ml four-necked flask equipped with a stirrer, thermometer and reflux condenser and to the suspension the united organic phases obtained according to the previous pharagraph are added at 45°-60° C. The reaction mixture is heated under weak reflux for an hour and filtered hot. The filtrate is poured back into the flask, which had been washed out previously, and stirred under water-cooling at about 20° C. for 2 hours. The reaction mixture is cooled to a temperature between −3° C. and 0° C. and subjected to crystallization for 3 hours. The precipitated crystals are filtered, washed twice with 50 ml of 95% aqueous methyl ethyl ketone and dried.

Thus 60 g of the desired compound are obtained in the form of yellowish-white crystals, yield 92%. According to the methods disclosed in Example 1 the product is identical with Depogen.H$_2$0.

EXAMPLE 3

Into a 500 ml three-necked flask equipped with a stirrer and thermometer 175 ml of water, 13.3 g (0.125 mole) of sodium carbonate and 35 ml of dichloro methane are weighed in, whereupon at 35° C. 43.3 g (0.1 mole) of No-Spa-hydrochloride are added under stirring. When all the solid substance is dissolved the phases are separated, and the aqueous layer is extracted with 15 ml of dichloro methane.

To 300 ml of isopropanol 37 ml of water and 22.6 g (0.095 mole) of theophylline-7-acetic acid are added and the dichloro-methane solutin of No-Spa base is added at 35° C. From the reaction mixture 100 ml of the solvent are distilled off, whereupon a mixture of 100 ml of isopropanol and 3 ml of water is added and the hot mixture is filtered, cooled to 10° C., allowed to crystallize for 2 hours. The crystals are filtered, washed with 100 ml of 95% acetone and dried.

Thus 52.5 g of the desired compound are obtained in the form of yellowish-white crystals, yield 83%. According to the methods described in Example 1 the product is identical with Depogen.H$_2$O.

EXAMPLE 4

Preparation of 1-(3',4'-diethoxy-benzyl)-6,7-diethoxy-3,4-dihydro-isoquinolinium-theophylline-7-acetate (referred to furtheron as Depogen)

Into a 250 ml four-necked flask equipped with a stirrer, thermometer and condenser 35 g of crystalline 1-(3',4'-diethoxy-benzyl)-6,7-diethoxy-3,4-dihydro-isoquinolinium-theophylline-7-acetate-monohydrate and 200 ml of ethanol are weighed in and the mixture is heated to boiling under stirring. A clear solution is formed, which is filtered and the hot filtrate is allowed to cool. 23.1 g of the desired compound precipitates in the form of a yellowish-white fibrous product, yield 95%. mp.: 152°-154° C.

According to a comparison of the elemental analysis and IR-spectra the product is identical with Depogen, purity 99.5%.

EXAMPLE 5

Preparation of 1-(3',4'-diethoxy-benzyl)-6,7-diethoxy-3,4-dihydro-isoquinolinium-theophylline-7-acetate Into a 250 ml four-necked flask equipped with a stirrer 25 g of 1-(3',4'-diethoxy-benzyl)6,7-diethoxy-3,4-dihydro-isoquinolinium-theophylline-7-acetate-monohydrate and 250 ml of anhydrous acetone are weighed in. The reaction mixture is stirred at room temperature for 5 hours. The crystalline product is transformed into a loose yellowish-white thick substance, which is filtered, washed twice with 20 ml of acetone each and dried. Thus 23.5 g of the desired compound are obtained, yield 96.5%. mp: 152°-154° C. The product is identical with the substance prepared according to Example 4.

What we claim is:

1. A process for the preparation of pure 1-(3',4'-diethoxybenzyl)-6,7-diethoxy-3,4-dihydroisoquinolinium-theophylline-7-acetate, free of contaminating oxidation products, which comprises the steps of:
    (a) preparing in situ a first solution of 1-(3',4'-diethoxybenzyl)-6,7-diethoxy-3,4-dihydroisoquinoline in a first organic solvent and water by adding 1-(3',4'-diethoxybenzyl)-6,7-diethoxy-3,4-dihydroisoquinoline hydrochloride and an alkali to the water and the first organic solvent;
    (b) removing water from the first solution formed in step (a);
    (c) preparing a second solution containing theophylline-7-acetic acid, water, and a second organic solvent, the molar amount of theophylline-7-acetic acid being about equal to the molar amount of 1-(3',4'-diethoxybenzyl)-6,7-diethoxy-3,4-dihydroisoquinoline hydrochloride used to form the first solution in step (a);

(d) combining the first and second solutions to form a reaction mixture and heating the reaction mixture;

(e) filtering the heated reaction mixture to form a hot filtrate;

(f) cooling the hot filtrate to precipitate crystals of 1-(3',4'-diethoxybenzyl)-6,7-diethoxy-3,4-dihydroisoquinoline-theophylline-7-acetate monohydrate;

(g) separating the precipitated crystals from the reaction mixture; and (h) dehydrating the precipitated crystals to form the desired product.

2. The process defined in claim 1 wherein the first organic solvent employed in step (a) and the second organic solvent employed in step (c) are the same organic solvent.

3. The process defined in claim 1 wherein the first organic solvent employed in step (a) and the second organic solvent employed in step (c) are different, and during step (d) the organic solvent is removed by distillation and replaced by an equal volume of the second organic solvent.

4. The process defined in claim 1 wherein the first organic solvent employed in step (a) is a water-miscible or water-immiscible organic solvent.

5. The process defined in claim 1 wherein the second organic solvent is a water-miscible organic solvent.

6. The process defined in claim 4 wherein the first organic solvent is a water-immiscible organic solvent, specifically dichloromethane.

7. The process defined in claim 4 wherein the first organic solvent is a water-miscible organic solvent, specifically a ketone or an alcohol.

8. The process defined in claim 5 wherein the second organic solvent is a ketone or an alcohol.

9. The process defined in claim 1 wherein in step (b) dehydration is carried out by thermal treatment.

10. The process defined in claim 1 wherein in step (b) dehydration is carried out by treatment with a solvent.

11. 1-(3',4'-diethoxy-benzyl)-6,7-diethoxy-3,4-dihydro-isoquinolinium-theophylline-7-acetate monohydrate.

12. Crystalline monohydrate of 1-(3',4'-diethoxy-benzyl)-6,7-diethoxy-3,4-dihydro-isoquinolinium-theophylline-7-acetate, or pure 1-(3',4'-diethoxy-benzyl)-6,7-diethoxy-3,4-dihydro-isoquinolinium-theophylline-7-acetate free of contaminating oxidation products whenever prepared by the process according to claim 1.

13. A process for the preparation of the crystalline monohydrate of 1-(3',4'-diethoxy-benzyl)-6,(7-diethoxy-3,4-dihydro-isoquinolinium-theophylline-7-acetate and if desired of pure 1-(3',4'diethoxybenzyl)-6,7-diethoxy-3,4-dihydro-isoquinolinium-theophylline-7-acetate free of contaminating oxidation products which comprises reacting 1-(3',4'-diethoxy-benzyl)-6,7-diethoxy-3,4-dihydro-isoquinoline with theophylline-7-acetic acid in the presence of water and one or more organic solvents, and if desired dehydrating the 1-(3',4'-diethoxy-benzyl)-6,7-diethoxy-3,4-dihydro-isoquinolinium-theophylline-7-acetate-monohydrate thus obtained.

* * * * *